United States Patent [19]

Dansereau et al.

[11] Patent Number: 5,049,374
[45] Date of Patent: Sep. 17, 1991

[54] ORAL (COATED BEAD) DOSAGE FORM FOR SODIUM IODIDE I-131

[76] Inventors: Richard J. Dansereau, R.D. 1 Box 162, Sherburne, N.Y. 13460; Raymond N. Dansereau, 275 S. Main Ave., Albany, N.Y. 12208

[21] Appl. No.: 441,984

[22] Filed: Nov. 28, 1989

[51] Int. Cl.$^5$ ................ A61K 43/00; C09K 11/04; A61N 5/00
[52] U.S. Cl. .................... 424/1.1; 252/645; 128/659
[58] Field of Search ............ 424/1.1; 252/645; 128/659; 600/3

[56] References Cited

U.S. PATENT DOCUMENTS 3,121,041  2/1964  Stern et al. ................... 424/1.1

Primary Examiner—John S. Maples
Assistant Examiner—Cynthia Harris

[57] ABSTRACT

A stabilized oral pharmaceutical bead dosage form of sodium iodide I-131 is described. The sodium iodide I-131 is dissolved in a polymer film and the polymer film is applied by conventional coating technology which affixes the sodium iodide I-131 to inert substrate beads. The film also stabilizes the sodium iodide I-131 from chemical degradation.

The utility of the bead dosage form is that it provides a decreased radiation hazard over that of handling a sodium iodide I-131 liquid. At the time of manufacture a specified amount of sodium iodide I-131 is applied to the substrate beads. The sodium idoide I-131 containing beads are then stored appropriately until dispensed by the pharmacist or physician. The key advantage of this system is that dispensing flexibility is maintained because as the sodium iodide I-131 undergoes radioactive decay the pharmacist or physician can compensate for the loss by dispensing a larger quantity of the coated beads to constitute the prescribed sodium iodide I-131 dose. Then just prior to patient administration, the beads can be filled into a single hard gelatin capsule of if the patient prefers, the beads can be dispensed in water, orange juice, apple sauce or any suitable liquid or food intended for oral administration.

This dosage form described herein minimizes the radiation hazard from the time of manufacture to the time of administration, provides dosing flexibility to the pharmacist and physician and offers the patient numerous options in terms of dosage form administration.

3 Claims, No Drawings

ORAL (COATED BEAD) DOSAGE FORM FOR SODIUM IODIDE I-131

INTRODUCTION

Sodium iodide I-131 is frequently used as a marker in nuclear medicine for radionuclide studies involving the human thyroid. It is also used to measure thyroid uptake of iodine, and it is the preferred radiopharmaceutical agent for the identification and assessment of ectopic thyroid tissue. Sodium iodide I-131 is an important adjunct in therapy for thyroid carcinoma for ablation of postsurgical residual thyroid tissue in the neck and eradication of functioning local and distant metastases (1). The doses of sodium iodide I-131 that are used in the treatment of hyperthyroidism and in thyroid carcinoma range from approximately 100 megabecquerels ($MB_q$) to several gigabecquerels ($GB_q$).

Sodium iodide I-131 is commercially available for oral administration in aqueous solution and capsule form (2). The liquid dosage form provides the pharmacist and physician with infinite flexibility in dose selection, but it presents significant radiation hazards association with spills; an additional hazard, unique to handling solutions containing sodium iodide I-131, is the inhalation of volatile components containing airborne radiation (3). In solution, sodium iodide can be oxidized to iodine gas by oxygen: $4HI + O_2 \rightarrow 2I_2 + 2H_2O$ (4). Exposure to light, heat, and other oxidizing agents, such as chloride ions found in tap water, can accelerate the oxidation of the iodide. Schlosser capsule dosage form is the lack of dosing flexibility of the filled capsules. Once the capsules are filled with the predetermined radioactivity it is not possible to alter the dose. This is a problem because the sodium iodide I-131 undergoes radiactive decay and the Stern and Schlosser capsules decrease in activity over time. The sodium iodide I-131 has a half life of 8.06 days, therefore, once the predetermined amount of sodium iodide is filled into the gelatin capsules it is not possible to change the amount of radioactivity, and dosing flexibility is lost because the dose is fixed and can't be individualized to the patient. This means that the physician will have to administer several capsules (usually 2-5) to constitute the correct dose of sodium iodide I-131. This is an inconvenience to the patient and often creates compliance issues.

A new dosage form that reduces the hazards of handling sodium iodide I-131 for the radiopharmacist and maintains dosing flexibility for the physician is needed. Rapidly dissolving beads, uniformly coated with a film that is impregnated with sodium iodide I-131, would meet these requirements. This patent describes the development of such a system.

DESCRIPTION OF INVENTION

The present invention (dosage form) described herein consists of sodium iodide I-131 that is first dissolved in a polymer film and then applied on inert substrate beads through conventional coating technology. As used herein, dosage form is the final composition used for oral administration to humans. In this application, the dosage form consists of the beads layered with a film containing sodium iodide I-131. As used herein, a polymer film is a polymer based layer used to affix the sodium iodide I-131 to the inert substrate beads. As used herein, beads are inert spherical shaped particles ranging in diameter from 250-2,000 microns which are used as substrate upon which the film containing sodium iodide I-131 is applied. The polymer film also stabilizes the sodium iodide from chemical degradation. The sodium iodide I-131 containing beads are then stored appropriately until dispensed by the pharmacist or the physician. The key advantage of this system is that dispensing flexibility is maintained because as the sodium iodide I-131 undergoes radioactive decay the pharmacist or physician can compensate for the decay by dispensing a larger quantity of the coated beads to constitute the prescribed sodium iodide I-131 dose. Then just prior to administration, the beads can be filled into a single gelatin capsule or if the patient prefers, the beads can be dispersed in water, orange juice. Upon oral administration to humans, the gelatin capsule shell is soluble in the gastrointestinal juice thereby exposing the beads. Upon exposure of the coated beads to the gastrointestinal juices the polymer releases the sodium iodide I-131 and the sodium iodide I-131 becomes available in the gastrointestinal tract for absorption into the systemic system.

The dosage form described herein minimizes the radiation hazard from the time of manufacture to the time of administration, provides dosing flexibility to the pharmacist and physician, and offers the patient numerous option in terms of dosage form administration.

In addition, the composition of the present invention may contain optional pharmaceutically acceptable components which may modify the dose forms physical characteristics. As used herein, a pharmaceutically acceptable component is one which is suitable for use with humans and/or other animals without undue adverse side effects (such as toxicity, irritation and allergic response).

ESSENTIAL COMPONENTS

Active Ingredient

The composition of the invention contains sodium iodide I-131 or sodium iodide I-123 as the active ingredient.

Inert Substrate Beads

The substrate bead is used as an inert substrate to which the sodium iodide I-131 containing polymer film is applied. The preferred composition of the beads is a mixture of one or more of the following: sucrose, mannitol, lactose, dextrose, sorbitol, cellulose or starch. The preferred mixture being sucrose and starch. The preferred size of the core beads is in the range of 250-2,000 microns. The most preferred are beads in the range of 400-700 microns.

Polymer Film

The major purpose of the polymer film is to affix the sodium iodide I-131 to the inert substrate beads. Since sodium iodide is a deliquescent material (it gradually picks up moisture in the air and will turn from dry drug crystals to a liquid), the film protects the sodium iodide from moisture pick up. Sodium iodide also becomes brown in the air because of the liberation of iodine, therefore, the polymer film also prevents this reaction.

The polymer film preferably comprises:
a) a mixture of hydroxypropylmethylcellulose and ethylcellulose (commercially available as Aquacoat, FMC Corporation).
b) a suitable plasticizer preferably dibutyl sebacate Film forming polymers, plasticizers and optional materials are described in the *Handbook of Pharmaceutical*

*Excipients* (5), incorporated by reference herein. Preferably the polymer or polymers mix can consist of any combination that offers protection against moisture pickup, oxygen transfer and which is designed for immediate release of the sodium iodide I-131 upon human ingestion (by exposure to gastrointestinal juices) Preferably, the polymer material is selected from the group consisting of cellulose ethers, polyvinylpyrrolidone, polyethyleneglycols, methacrylic acid/methacrylic acid ester copolymers and mixtures thereof. Preferred are mixtures of cellulose ethers particularly hydroxypropylmethylcellulose, hydroxypropylcellulose and ethylcellulose. Particularly preferred is a mixture of ethylcellulose and hydroxypropylmethylcellulose. The preferred weight of the applied film on the substrate beads is between 5-25% (weight gain). The most preferred weight is from 5-10% (weight gain).

Plasticizers useful in the film include, for example, polyethyleneglycol, glycerin, propylene glycol, triacetin, acetylated monoglycerides, phthalate esters, caster oil, dibutyl sebacate and selected mixtures thereof. The preferred amount of plasticizer is 5-40% to that of the polymer. The most preferred weight is 20-40%.

In addition to sodium iodide I-131, polymer film former and plasticizers the film may contain optional fillers, pigments, and dyes. Such fillers include sucrose, kaolin, talc, magnesium stearate, titanium dioxide and mixtures thereof. Such dyes and pigments include those normally used in the pharmaceutical industry.

The amount of sodium iodide I-131 applied to the beads in the film may vary depending upon the concentration desired in the finished product. Preferably the concentration of sodium iodide I-131 in the finished product is from several megabecquerels to several gigabecquerels per 1 gram of beads. The amount of sodium iodide containing polymer film applied to the beads is a function of the particular polymer present in the film.

METHODS

The compositions of this invention may be made by standard particle coating devices with appropriate lead shielding. The following are non-limiting examples of compositions and methods for the manufacture of the dosage form.

EXAMPLE 1

| Substrate Beads - | Size: | 710-840 microns |
| --- | --- | --- |
| | Weight: | 600 grams |

| Polymer Film | |
| --- | --- |
| Ingredient | Amount (% w/w) |
| Hydroxypropylmethylcellulose E5 (10% in water) | 23.1 |
| Distilled Water | 34.7 |
| Ethylcellulose (Aquacoat dispersion FMC Corp) | 38.6 |
| Dibutyl Sebacate | 2.8 |
| Sodium Iodide I-131* | — |
| FD&C Red #3 Dye | .8 |
| | 100% |

*weight of sodium iodide I-131 is negligible.

1) A 10% w/w hydroxypropylmethylcellulose (HPMC) E5 solution was prepared in distilled water and deaerated overnight at 5° C.
2) The Aquacoat (FMC) was plasticized with dibutyl sebacate. The dibutyl sebacate was added to the Aquacoat and mixed for 30 minutes with a Lightnin mixer.
3) The sodium iodide I-131 was dissolved in a portion of the distilled water and added to the HPMC solution.
4) FD&C Red #3 dye was added with mild agitation to the HPMC solution.
5) The HPMC mixture was added to the Aquacoat mixture and mixed for 20 minutes before coating and throughout the coating process.

Using appropriate lead shielding, 600 g of the 710-840 microns beads were coated in a fluidized-bed coating column with an inlet coating temperature of 50° C. The sodium iodide polymer film was pumped at a rate of 6 g/min into the atomizer, which operated at a spray pressure of 2 atmospheres and had a spray-nozzle orifice of 1.1 mm. After coating, the beads were dried on trays at 45° C. for 24 hours.

EXAMPLE 2

| Substrate Beads - | Size: | 590-840 microns |
| --- | --- | --- |
| | Weight: | 500 grams |

| Polymer Coating | |
| --- | --- |
| Ingredient | Amount (% w/w) |
| Methacrylic acid ester copolymers (Eudragit E-100) | 8 |
| Acetone | 24 |
| Isopropyl Alcohol | 56 |
| Polyethylene Glycol 3350 | 2 |
| FD&C Yellow #6 Dye | .02 |
| Titanium Dioxide | 1.4 |
| Purified Water | 8.6 |
| Sodium Iodide I-131* | — |
| | 100% |

*The weight of sodium iodide I-131 is negligible.

The composition is made by a method essentially similar to that in Example 1.

EXAMPLE 3

| Core Beads - | Size: | 800-1,000 microns |
| --- | --- | --- |
| | Weight: | 600 grams |

| Polymer Coating | |
| --- | --- |
| Ingredient | Amount (% w/w) |
| Hydroxypropylcellulose E5 | 10 |
| Polyvinylpyrrolidine | 5 |
| Distilled Water | 76.9 |
| Polyethylene Glycol 8000 | 4 |
| Talc | 4.0 |
| Blue Dye | .1 |
| Sodium Iodide I-131* | — |
| | 100% |

*The weight of sodium iodide I-131 is negligble.

The composition is made by a method essentially similar to that in Example 1.

REFERENCES CITED

1) Mettler, F.A. and Guiberteau, M.J., Thyroid and parathyroid. In *Essentials of Nuclear Medicine Imaging*, 2nd Edition, Harcourt Brace Javanovich, Orlando, 1986, pp. 89-115.
2) United States Pharmacopeia, National Formulary USP XXII, NF XVII, The United States Pharmacopeial Convention, Inc., 12601 Twinbrook Parkway, Rockville, Md. 20852 pp. 709-710, 1990.
3) Haenchen, M., Eichling, J. and Glasgow, G., Assessment of the airborne activity levels during I-131 thyroid therapies. Poster presented at the *30th Annual Health Physics Society Meeting*, Chicago, June 1985.

4) Howard, B.Y., Safe handling of radioiodinated solutions. *J. Nucl. Med. Technol.*, 4 (1986) 28–30.
5) Handbook of Pharmaceutical Excipients, Published by the American Pharmaceutical Association, 2215 Constitution Ave., NW, Washington, D.C. 20037, 1980.

What is claimed is:

1. A coated bead pharmaceutical composition for oral administration comprising:
   a) inert substrate beads
   b) a polymer film
   c) and a radioactive species of sodium iodide wherein said sodium iodide is uniformly dispersed in said polymer film; wherein said polymer film is affixed to said inert substrate beads.

2. The composition of claim 1 wherein said radioactive species of sodium iodide is sodium iodide I-131.

3. The composition of claim 1 wherein said radioactive species of sodium iodide is sodium iodide I-123.

* * * * *